United States Patent [19]

Allison

[11] 4,182,346
[45] Jan. 8, 1980

[54] ELECTRODE

[75] Inventor: Kenneth C. Allison, Crystal Lake, Ill.

[73] Assignee: Biomedical International Company, River Grove, Ill.

[21] Appl. No.: 802,715

[22] Filed: Jun. 2, 1977

[51] Int. Cl.$^2$ ............................................... A61B 5/04
[52] U.S. Cl. .................................................... 128/641
[58] Field of Search ............. 128/2.06 E, 2.1 E, 404, 128/410, 411, 416–418, 155, 156, DIG. 4, 639–641, 783, 798, 802, 803

[56] References Cited

U.S. PATENT DOCUMENTS

| | | | |
|---|---|---|---|
| 3,550,589 | 12/1970 | Wallerstein | 128/156 |
| 3,834,373 | 9/1974 | Sato | 128/2.06 E |
| 3,841,312 | 10/1974 | Corasanti | 128/2.06 E |
| 3,862,633 | 1/1975 | Allison et al. | 128/2.06 E |
| 3,865,099 | 2/1975 | Robichaud | 128/2.06 E |
| 3,888,247 | 6/1975 | Stenvall | 128/155 |
| 3,945,384 | 3/1976 | Allison et al. | 128/2.06 E |
| 3,967,628 | 7/1976 | Vredenbregt | 128/417 |
| 4,090,752 | 5/1978 | Long | 128/2.06 E X |

FOREIGN PATENT DOCUMENTS 2440836 3/1976 Fed. Rep. of Germany ....... 128/2.1 E

*Primary Examiner*—Lee S. Cohen

[57] ABSTRACT

A biomedical electrode for use with a signal receiving apparatus is disclosed herein. The electrode includes an open-sided resilient container having a permeable diaphragm closing the open side. A terminal plug is positioned in connection with the resilient container. An electrolyte is contained in the container, and permeates the permeable diaphragm. A flat closed-cell perforated flexible annular mounting pad surrounds the container, and is secured to it. A flexible stainless steel ring engages the resilient container, and secures the flat closed-cell perforated flexible annular mounting pad in fixed engagement with a flange of the container. A uniform adhesive is secured to a side of the flat closed-cell perforated flexible annular mounting pad adjacent the permeable diaphragm for adhesively securing the electrode to the surface of a subject. The resilient container and flat closed-cell perforated flexible annular mounting pad are releasably mounted on a release paper and diaphragm sealer.

4 Claims, 4 Drawing Figures

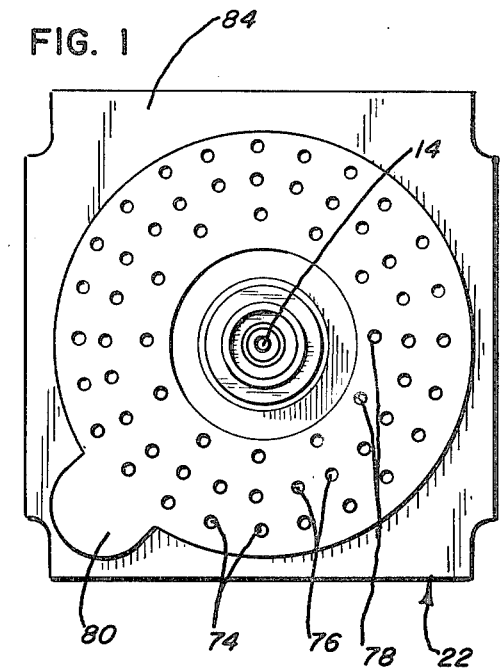
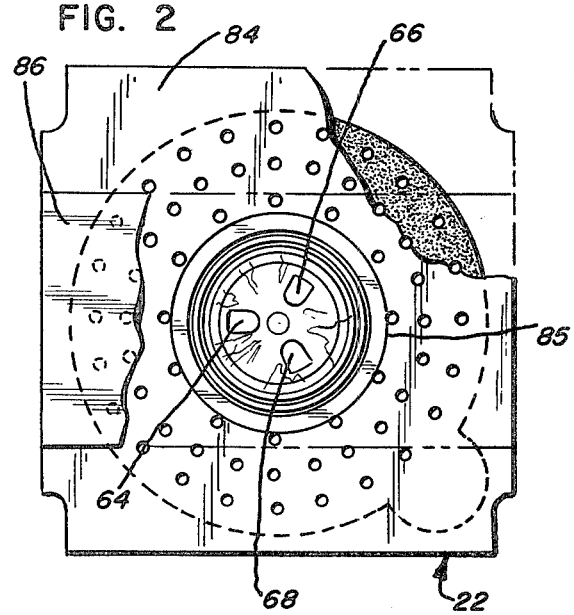
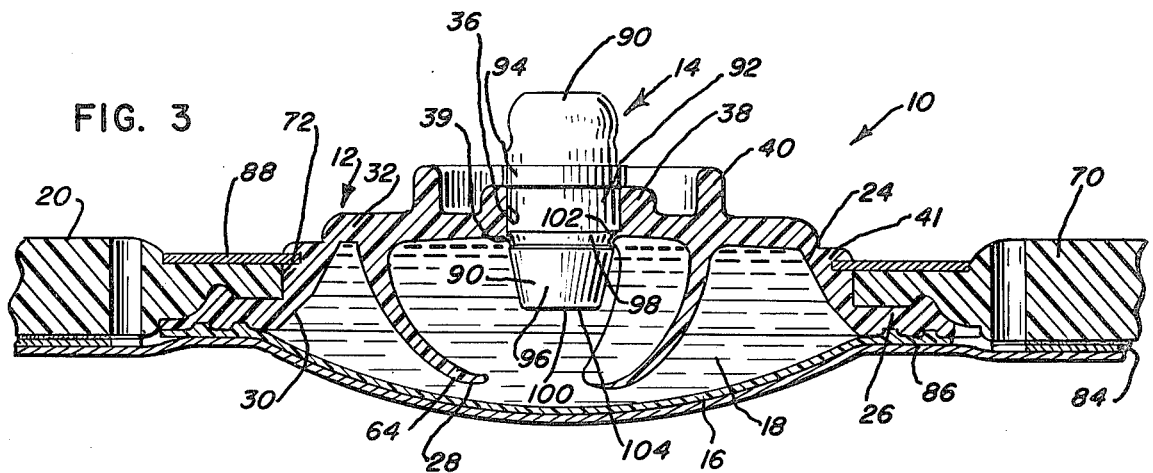
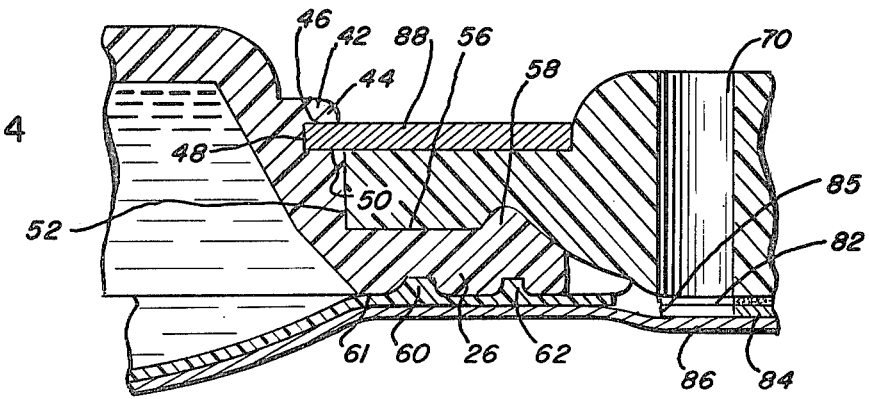

ELECTRODE

BACKGROUND OF THE INVENTION

The general construction of biomedical electrodes of this general type is described in U.S. Pat. No. 3,973,557, issued Aug. 10, 1976, to Kenneth C. Allison.

Biomedical electrodes are used in direct contact with skin surfaces of subjects. When a biomedical electrode is applied to the skin of a subject, the subject may perspire under the electrode. Perspiration formed under the diaphragm of a biomedical electrode employing a liquid electrolyte simply mixes with electrolyte, which permeates the diaphragm. Perspiration is also released under the electrode mount as well. In order to maintain the comfort of the subject, as well as adhesive connection of the mount with the skin, it is desirable that the moisture from the perspiration is released from the electrode mount. One method of releasing the moisture is disclosed in U.S. Pat. No. 3,973,557 to Allison. An open-cell foam, having a network adhesive, is employed for the electrode mount. The moisture migrates past the network adhesive, through the pores of the open-cell foam, and evaporates from the top of the mount. Open-cell foams are, however, somewhat more expensive than closed-cell foams. Likewise, network adhesive is somewhat more expensive to purchase and to apply than a uniform adhesive.

It is also apparent that the electrode mount must be secured to the container. One method of securing the electrode mount to the container is by heat sealing. Both the electrode mount and the container are composed of plastic, which can be fused together by heat sealing. Heat sealing of the foam mounting pad to the container can be a delicate operation. The sealing temperature must be carefully controlled. If the temperature is too high, the mounting pad will melt and tear. If the temperature is too low, the heat sealing will not be complete.

What is needed, then, is an electrode which uses relatively inexpensive closed-cell foam mounting pads and uniform adhesive while allowing perspiration to evaporate from a subject. In addition, the electrode mount should be secured to the container by a mechanical lock.

SUMMARY OF THE INVENTION

The present electrode is a specific improvement of the electrode disclosed in U.S. Pat. No. 3,973,557. The subject electrode has an improved electrode mount construction, wherein the electrode mounting pad is composed of a perforated closed-cell foam material, shaped in an annular ring. A continuous adhesive is applied to the lower portion of the mounting pad. A stainless steel ring forceably secures the electrode mounting pad to a container flange of a resilient container. The electrode mounting pad is mounted, ready for use on release paper and diaphragm sealer. The container also has a filling aperture in its center. A microporous permeable diaphragm is secured to one side of the container to seal the container closed. An electrolyte is introduced into the container through the filling aperture to fill the container.

It is therefore a principal object of the present invention to provide an improved biomedical electrode construction, which utilizes a mounting pad composed of a perforated closed-cell foam.

It is another object of the instant invention to provide an improved biomedical electrode construction, having a uniform adhesive applied to the electrode mounting pad.

It is a further object of the instant invention to provide an improved biomedical electrode in which the mounting pad is lockingly secured with the resilient container by a flexible annular ring.

Other objects and uses of this invention will become obvious to one skilled in the art upon a perusal of the following specifications and claims in light of the accompanying drawing.

BRIEF DESCRIPTION OF THE DRAWING

FIG. 1 is a top view of a biomedical electrode, in contact with a release paper backing, embodying the present invention;

FIG. 2 is a bottom view of the biomedical electrode of FIG. 1, having portions of the release paper and a foil diaphragm broken away to show details thereof;

FIG. 3 is an enlarged cross-sectional view of the electrode of FIG. 1, with portions broken away to show better the interior construction thereof; and FIG. 4 is an enlarged side elevational view similar to FIG. 3, showing details of an electrode mount in locking connection with an annular lock ring and a container.

DESCRIPTION OF THE PREFERRED EMBODIMENT

Referring now to the drawing, and especially to FIG. 3, a biomedical electrode which is a specific embodiment of the instant invention is shown therein, and is generally indicated by numeral 10. The biomedical electrode 10 generally includes a resilient open-sided container 12. A terminal plug 14 is sealingly mounted in container 12. A microporous diaphragm 16 is sealingly mounted on an open side of container 12. An electrolyte 18 is held within the container by diaphragm 16. An electrode mount 20 is secured to the outer periphery of container 12. Container 12 and electrode mount 20 are mounted on a release backing 22.

Container 12 is composed of a semi-transparent polypropylene, which is resilient and may be conveniently manufactured by injection molding. It is readily apparent that any other suitable transparent material may be used. The container generally consists of three integral parts, namely: a cup 24; a flange 26, formed integral with the cup; and a resilient diaphragm support 28. Cup 24 includes a beveled sloping wall 30, with a top 32 formed integral therewith. In the center of top 32, there is a filling aperture 36, with a terminal boss 38 formed integral with the top and concentric with the filling aperture 36. A resilient annular sealing flange 39 is formed integral with top 32. Flange 39 extends inward to the filling aperture 36 for engagement with terminal plug 14. A terminal annulus 40 surrounds the boss 38, and is formed integral with top 32. A ring lock 41 is formed integral with cup 24. Ring lock 41 includes an upper ring shoulder 42, having a curved ring bead 44 and a flat ring face 46. Ring shoulder 42 is an annular ring shoulder. A ring wall 48 is formed integral with, and perpendicular to, ring face 46. Ring wall 48 is positioned interiorly of ring bead 44. A lower ring shoulder 50 is formed integral with, and perpendicular to, ring wall 48, opposite ring face 46. Lower ring shoulder 50 and ring face 46 are parallel. Ring shoulder 50 extends slightly past upper ring shoulder face 46. A vertical wall 52 is formed integral with, and perpendicular to, ring shoulder 50.

Flange 26 is formed integral with the lower portion of sloping wall 30. A pad face 56 is formed integral with, and perpendicular to, vertical wall 52. An annular pad bead 58 is formed integral with pad face 56. An annular groove 60 is formed into the flange adjacent to the cup, thereby defining a substantially flat diaphragm ring 61 on the side opposite to the pad face. An annular sealing groove 62 is formed into flange 26, adjacent to annular groove 60.

Resilient diaphragm support 28 includes three identical resilient fingers 64, 66 and 68 formed integral with the interior of top 32. Each of the resilient fingers has one end formed integral with top 32. Each of the fingers extends outward of the container, and is curved toward the axis of filling aperture 36. The fingers extend beyond the container to engage diaphragm 16. Each finger has a rounded end, and is tapered to increase the resilience of the finger. The fingers are equiangularly spaced about the filling aperture, so that the terminal plug is surrounded by the resilient fingers.

Electrode mount 20 includes a thin piece of closed-cell polyethylene foam pad 70, having a thickness of 3.18 millimeters. Pad 70 has a circular container aperture 72 in its center, and receives a portion of container 12 therein. An outside concentric circle of apertures 74 has a plurality of 2.38 millimeter diameter right circular cylindrical perforations extending through pad 70. The perforations of concentric circle 74 are spaced at 15° intervals about aperture 72. A middle concentric circle of apertures 76 lies inside circle 74, and has a plurality of 2.38 millimeter diameter right circular cylindrical perforations extending through pad 70. The perforations of circle 76 are also positioned at 15° intervals about central aperture 72. An inside concentric circle of apertures 78 has a plurality of 2.38 millimeter diameter right circular cylindrical perforations extending through pad 70. The perforations of circle 78 are positioned at 30° intervals about central container aperture 72. The diameter of the perforations of all concentric circles can range between 0.40 millimeters and 6.35 millimeters, although 2.38 millimeters is employed in the preferred embodiment. A pull tab 80 is formed integral with pad 70. An adhesive 82 in a layer having a uniform thickness is secured to one side of the polyethylene foam pad.

Release backing 22 includes a conventional release paper 84, positioned over adhesive 82 to prevent the adhesive from sticking to undesired materials. Release paper 84 is an elongated rectangular paper, perforated at regular intervals to allow sections to be removed. A large diaphragm aperture 85 is formed in release paper 84. An elongated rectangular sealing sheet 86, which is composed of aluminum foil having an adhesive thereon, is releaseably mounted in sealing engagement with annular sealing groove 62 of the container to prevent electrolyte 18 from drying out in storage. Sealing sheet 86 has a width less than its length. When electrode 10 is in use, sealing sheet 86 is removed so that the diaphragm may contact the surface of the subject.

Pad 70 is secured to flange 26 by a circular annular stainless steel flat lock ring 88. Annular stainless steel ring 88 is held in ring lock 41, which is formed integral with container 12 above flange 26. It should be noted that ring lock 41 lies in a plane parallel to flange 26. Annular stainless steel ring 88 has a width substantially larger than its thickness. The distance between stainless steel lock ring 88 and pad face 56 of flange 26 is 1.14 millimeters. The distance between stainless steel lock ring 88 and pad bead 58 is 0.76 millimeters. Stainless steel lock ring 88 extends past pad bead 58. Mounting pad 20 is secured between lock ring 88 and flange 26.

Terminal plug 14 generally includes a terminal head 90, with a terminal body 92 formed integral therewith, and a terminal flange 94 between the head and the body. The terminal head 90 is adapted for receipt of a conventional terminal connector. The body 92 includes a root portion 96, formed integral with flange 94. Root portion 96 is formed integral with a neck 98, which neck has a tapered nose 100 formed integral therewith. The tapered nose 100 has a shoulder 102 adjacent to the neck 98, and a flat nose 104 on its free end.

The electrolyte, in this instance, is a physiological saline solution, including a wetting agent; a bacteria inhibitor; and glycerine to limit the evaporation of the electrolyte. The electrolyte is contained in the container by diaphragm 16 which, in this instance, is a thin sheet of microporous polypropylene, so that the diaphragm is wetted by the electrolyte.

The electrode is assembled by heat sealing diaphragm 16 to the diaphragm ring 61, and securing electrode mount 20 to flange 26. Pad 70 has its central aperture 72 fitted about vertical wall 52. Pad 70 engages pad face 56 and bead 58 of flange 26. Annular stainless steel lock ring 88 is hot-forced into engagement with ring bead 44, walls 46, 48 and 50 of ring lock 41. Since lower ring shoulder 50 extends past upper wall 48, annular stainless steel ring 88 can be easily forced over the curved surface of ring bead 44; but will be stopped from further travel toward flange 26 by the slightly greater extension of ring shoulder 50. Thus, the stainless steel lock ring 88 cannot be inadvertently forced past ring lock 41. The lock ring 88 thus can be quickly and easily snapped into ring lock 41 by a relatively unskilled operator. Lock ring 88 thus compresses pad 70 to a thickness of 1.14 millimeters above pad face 56, and to a thickness of 0.76 millimeters at pad bead 58. The thickness of pad 70 is thus compressed to a minimum between pad bead 58 and lock ring 88. Any force applied to mounting pad 70 which tends to pull it away from container 12 will also tend to pull the foam at pad bead 58. The comparatively small separation between pad bead 58 and lock ring 88 prevents the foam adjacent pad face 56 from being pulled away from lock ring 88 and pad bead 58. The slight extension of lock ring 88 past pad bead 58 also serves to secure lockingly the pad 70 to pad bead 58. Thus, forces tending to pull pad 70 away from container 12 simultaneously pull pad 70 into stronger connection with pad bead 58 and lock ring 88. Pad 70 is thereby lockingly secured to container 12. There is no necessity for using delicate heat sealing techniques since the pad 70 is lockingly secured to container 12 by stainless steel ring 88.

Release paper 84 is placed over the pad 70. Diaphragm aperture 85 receives diaphragm 16. Release paper 84 is releasably connected to pad 70. Circles of perforations 74, 76 and 78 are punched through pad 70 and release paper 84 simultaneously. Sealing sheet 86 is then secured to release paper 84, and sealingly encloses diaphragm 16. Cup 24 is filled with electrolyte 18 through the filling aperture 36 in a manner such that all of the air is expelled from the container. Once the cup is sufficiently filled with electrolyte, terminal plug 14 is inserted into the filling aperture to seal closed the filling aperture.

The terminal plug is inserted into the filling aperture, with the longitudinal axis of the terminal plug and the filling aperture being aligned. The terminal plug is then forced down into the filling aperture 36. As the terminal plug moves through the filling aperture, the material of the container is pushed outward as it seals flange 52. The terminal plug is pushed down until flange 94 rests on the aperture boss 38. The container, being in tight engagement with the terminal plug, holds the terminal plug in sealing relationship. Once the terminal plug is in position, it may be seen that it is surrounded by resilient fingers 64, 66 and 68.

The terminal plug is composed of a suitable metal. The outer surface of the diaphragm is wetted by the electrolyte. A low electrical potential is established across the diaphragm and terminal to start a half cell reaction between the terminal plug and the chloride ions of the electrolyte.

The electrode is applied to the skin of the subject by removing the release paper 84 from pad 70, and simultaneously removing the sealing sheet 86 from diaphragm 16. The electrode is adhesively secured to the subject by positioning the electrode in a desired location and applying a load to pad 70. Diaphragm 16 is secured in contact with the surface of the subject. Inasmuch as diaphragm 16 is microporous, the electrolyte 18 permeates the diaphragm to wet slightly the exterior surface of the diaphragm. When the diaphragm is placed into contact with the subject's skin, good contact is made between the diaphragm and the subject's skin fluids without the use of any other material or scraping of the subject's skin. The electrolyte has an opportunity to unite with the natural skin fluids, thereby setting up a direct electrical connection between the lowest layer of the skin and the electrolyte.

Appropriate measurements may be taken in a conventional fashion, using conventional equipment. Electrical condition is observed on conventional electrical measuring equipment. There is a faithful reproduction of the signal through the electrolyte, united with the skin fluids, to provide a conductive path directly beneath the electrode in the lower layer of the patient's skin to the diaphragm to affect the half cell.

The electrolyte is a physiological saline solution, thus allowing the electrode to remain on the patient's skin for a long period of time. It should further be noted that, in the event that there is any evaporation of the electrolyte from the container, the resilient fingers keep the diaphragm extended outward from the container so that the diaphragm is in good electrical contact with the skin of the patient. The three resilient fingers also form a protective shield around the terminal so that, should a careless operator handle the electrode, the diaphragm would not be punctured on the terminal inasmuch as the resilient fingers would give pursuant to any abnormal pressure on the resilient fingers.

Since the patient may perspire, the plurality of perforations 74, 76 and 78 of pad 70 allow perspiration to pass through the pad. The perspiration is thereby evaporated without irritating the skin of the patient. The size and spacing of the perforations allows evaporation of perspiration, while the pad remains securely attached to the patient. Furthermore, the closed-cell electrode mounting pad, together with the continuous uniform adhesive, allows for uniform adhesion to the patient's skin, even if the patient happens to be perspiring. Thus, a relatively inexpensive closed-cell foam pad and uniform adhesive may be employed in the electrode mount of the present invention to allow evaporation of perspiration from the patient's skin.

The annular stainless steel ring securely locks the electrode mounting pad to the retaining cup without the necessity of heat sealing. The annular lock ring provides for easy assembly of the electrode since the electrode mount is secured to the container by simply snapping the lock ring into the container ring lock. The tab formed integral with the electrode mount allows quick and easy removal of the electrode from the release backing. The electrode may be simply and easily discarded by simply pulling the pad off the patient and discarding the entire electrode.

Although a specific embodiment of the present biomedical electrode has been shown and described in detail above, it is readily apparent that those skilled in the art may make various modifications and changes in the specific disclosure contained herein without departing from the spirit and scope of the present invention. It is to be expressly understood that the instant invention is limited only by the appended claims.

What is claimed is:

1. A biomedical electrode for use on a subject comprising: a container having an open side; an electrolyte in the container; a terminal mounted in engagement with the container extending exteriorly therefrom and being in electrical connection with the electrolyte; a substantially rigid lock ring secured to said container; an electrode mount secured to said container by the lock ring adjacent to the open side of the container; said container has a circular cross-section and the electrode mount is annular, said lock ring is an annular circular lock ring which engages said electrode mount, and an annular ring lock bead formed in said container, said ring lock bead engaging the lock ring and having an outer diameter slightly greater than the inner diameter of the lock ring to lock the lock ring into position.

2. A biomedical electrode for use on a subject as defined in claim 1, in which said annular circular lock ring is a substantially flat stainless steel annular circular lock ring, having a width substantially greater than a thickness.

3. A biomedical electrode for use on a subject comprising: a container having an open side; an electrolyte in the container; a terminal mounted in engagement with the container extending exteriorly therefrom and being in electrical connection with the electrolyte; a substantially rigid lock ring secured to said container; an electrode mount secured to said container by the lock ring adjacent to the open side of the container; said container has an outwardly extending annular flange; said lock ring is positioned adjacent to said flange of the container; said electrode mount being positioned between said lock ring and said flange, said electrode mount being secured in compression by said lock ring and said flange; said flange includes a pad face in engagement with the electrode mount, a pad bead on said pad face of the flange separated from said lock ring by a distance less than a distance which the pad face of said flange is separated from the lock ring.

4. A biomedical electrode for use on a subject comprising: a resilient polypropylene container having an open side, an annular ring lock bead formed integral with and exteriorally of said resilient polypropylene container opposite a flange formed integral with and exteriorally of said container parallel to said ring lock bead, said flange having a pad bead; a thin microporous diaphragm sealingly secured to the resilient polypropylene container enclosing said open side; an electrolyte in the container in contact with the thin microporous diaphragm permeating the thin microporous diaphragm to wet an outside surface of the subject; said container having a terminal plug mounted in sealing engagement with the container and extending outwardly thereof and having a portion in contact with the electrolyte to form a half cell therewith; a perforated annular closed-cell polyethylene foam electrode mount secured to said flange of said resilient container, said perforated annular closed-cell polyethylene foam electrode mount having a plurality of concentric circles of perforations, each of said perforations of said plurality of concentric circles of perforations defining circular cylinders having a diameter of 2.38 millimeters, each of said perforations extending through the electrode mount, said perforated annular closed-cell polyethylene foam electrode mount having a layer of adhesive having a uniform thickness covering a side of said perforated closed-cell polyethylene foam electrode mount adjacent to said thin microporous diaphragm, a circular stainless steel annular lock ring lockingly engaging said ring lock bead securing said perforated closed-cell polyethylene foam electrode mount to said resilient polypropylene container, said lock ring having an interior diameter slightly less than the outer diameter of the ring lock bead to be locked by the ring lock bead after being forced over the ring lock bead, said perforated annular closed-cell polyethylene foam electrode mount being compressed between said circular stainless steel annular lock ring and said pad bead on the flange; release paper releasably adhesively connected to said uniform adhesive, said release paper having a diaphragm aperture formed therein, said diaphragm aperture receiving said thin microporous diaphragm; and a diaphragm sealing strip, being composed of a thin sheet of aluminum foil, said diaphragm sealing strip sealingly enclosing said thin microporous diaphragm, said diaphragm sealing strip having a width less than a width of said release paper.

* * * * *